(12) United States Patent
Gale et al.

(10) Patent No.: US 8,114,150 B2
(45) Date of Patent: *Feb. 14, 2012

(54) RGD PEPTIDE ATTACHED TO BIOABSORBABLE STENTS

(75) Inventors: David C. Gale, San Jose, CA (US); Bin Huang, Pleasanton, CA (US); Kleine Klaus, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 11/453,679

(22) Filed: Jun. 14, 2006

(65) Prior Publication Data

US 2007/0293941 A1  Dec. 20, 2007

(51) Int. Cl.
*A61F 2/06* (2006.01)
(52) U.S. Cl. ............ 623/1.38; 623/1.42; 623/1.46
(58) Field of Classification Search ............ None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,213,580 A | 5/1993 | Slepian et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |

(Continued)

FOREIGN PATENT DOCUMENTS

DE   42 24 401   1/1994

(Continued)

OTHER PUBLICATIONS

Steadman's Medical Dictionary, 27th Ed. (Lippincott Williams, 2000, definition of "amphipathic").*

(Continued)

*Primary Examiner* — Cherie M Woodward
(74) *Attorney, Agent, or Firm* — Squire Sanders (US) LLP

(57) ABSTRACT

Provided herein is a medical device that includes RGD attached to the device via a spacer compound.

28 Claims, 1 Drawing Sheet

U.S. PATENT DOCUMENTS

| | | | |
|---|---|---|---|
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,383,928 A | 1/1995 | Scott et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,575,815 A | 11/1996 | Slepian et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,607,475 A | 3/1997 | Cahalan et al. |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,725,568 A | 3/1998 | Hastings |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,782,908 A | 7/1998 | Cahalan et al. |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,843,156 A | 12/1998 | Slepian et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,874,165 A | 2/1999 | Drumheller |
| 5,876,433 A | 3/1999 | Lunn |
| 5,877,224 A | 3/1999 | Brocchini et al. |
| 5,879,713 A | 3/1999 | Roth et al. |
| 5,891,192 A | 4/1999 | Murayama et al. |
| 5,897,955 A | 4/1999 | Drumheller |
| 5,902,875 A | 5/1999 | Roby et al. |
| 5,905,168 A | 5/1999 | Dos Santos et al. |
| 5,910,564 A | 6/1999 | Gruning et al. |
| 5,914,182 A | 6/1999 | Drumheller |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,087,479 A | 7/2000 | Stamler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,174,539 B1 | 1/2001 | Stamler et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,379 B1 | 4/2002 | Wang |
| 6,379,381 B1 | 4/2002 | Hossainy et al. |
| 6,379,382 B1 | 4/2002 | Yang |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,471,978 B1 | 10/2002 | Stamler et al. |
| 6,475,779 B2 | 11/2002 | Mathiowitz et al. |
| 6,482,834 B2 | 11/2002 | Spada et al. |
| 6,494,862 B1 | 12/2002 | Ray et al. |
| 6,497,729 B1 | 12/2002 | Moussy et al. |
| 6,503,538 B1 | 1/2003 | Chu et al. |

| | | | | | |
|---|---|---|---|---|---|
| 6,503,556 B2 | 1/2003 | Harish et al. | 2001/0037145 A1 | 11/2001 | Guruwaiya et al. |
| 6,503,954 B1 | 1/2003 | Bhat et al. | 2002/0005206 A1 | 1/2002 | Falotico et al. |
| 6,506,408 B1 | 1/2003 | Palasis | 2002/0007213 A1 | 1/2002 | Falotico et al. |
| 6,506,437 B1 | 1/2003 | Harish et al. | 2002/0007214 A1 | 1/2002 | Falotico |
| 6,514,734 B1 | 2/2003 | Clapper et al. | 2002/0007215 A1 | 1/2002 | Falotico et al. |
| 6,524,347 B1 | 2/2003 | Myers et al. | 2002/0051730 A1 | 5/2002 | Bodnar et al. |
| 6,527,801 B1 | 3/2003 | Dutta | 2002/0077693 A1 | 6/2002 | Barclay et al. |
| 6,527,863 B1 | 3/2003 | Pacetti et al. | 2002/0082679 A1 | 6/2002 | Sirhan et al. |
| 6,528,526 B1 | 3/2003 | Myers et al. | 2002/0087123 A1 | 7/2002 | Hossainy et al. |
| 6,530,950 B1 | 3/2003 | Alvarado et al. | 2002/0091433 A1 | 7/2002 | Ding et al. |
| 6,530,951 B1 | 3/2003 | Bates et al. | 2002/0111590 A1 | 8/2002 | Davila et al. |
| 6,540,776 B2 | 4/2003 | Sanders Millare et al. | 2002/0165601 A1 | 11/2002 | Clerc |
| 6,544,223 B1 | 4/2003 | Kokish | 2002/0165608 A1 | 11/2002 | Llanos et al. |
| 6,544,543 B1 | 4/2003 | Mandrusov et al. | 2002/0176849 A1 | 11/2002 | Slepian |
| 6,544,582 B1 | 4/2003 | Yoe | 2002/0183581 A1 | 12/2002 | Yoe et al. |
| 6,555,157 B1 | 4/2003 | Hossainy | 2002/0188037 A1 | 12/2002 | Chudzik et al. |
| 6,558,733 B1 | 5/2003 | Hossainy et al. | 2002/0188277 A1 | 12/2002 | Roorda et al. |
| 6,565,659 B1 | 5/2003 | Pacetti et al. | 2003/0004141 A1 | 1/2003 | Brown |
| 6,572,644 B1 | 6/2003 | Moein | 2003/0028243 A1 | 2/2003 | Bates et al. |
| 6,585,755 B2 | 7/2003 | Jackson et al. | 2003/0028244 A1 | 2/2003 | Bates et al. |
| 6,585,765 B1 | 7/2003 | Hossainy et al. | 2003/0032767 A1 | 2/2003 | Tada et al. |
| 6,585,926 B1 | 7/2003 | Mirzaee | 2003/0036794 A1 | 2/2003 | Ragheb et al. |
| 6,605,154 B1 | 8/2003 | Villareal | 2003/0039689 A1 | 2/2003 | Chen et al. |
| 6,613,082 B2 | 9/2003 | Yang | 2003/0040790 A1 | 2/2003 | Furst |
| 6,613,084 B2 | 9/2003 | Yang | 2003/0059520 A1 | 3/2003 | Chen et al. |
| 6,613,432 B2 | 9/2003 | Zamora et al. | 2003/0060877 A1 | 3/2003 | Falotico et al. |
| 6,616,765 B1 | 9/2003 | Hossaony et al. | 2003/0065377 A1 | 4/2003 | Davila et al. |
| 6,620,617 B2 | 9/2003 | Mathiowitz et al. | 2003/0072868 A1 | 4/2003 | Harish et al. |
| 6,623,448 B2 | 9/2003 | Slater | 2003/0073961 A1 | 4/2003 | Happ |
| 6,623,521 B2 | 9/2003 | Steinke et al. | 2003/0083646 A1 | 5/2003 | Sirhan et al. |
| 6,625,486 B2 | 9/2003 | Lundkvist et al. | 2003/0083739 A1 | 5/2003 | Cafferata |
| 6,641,611 B2 | 11/2003 | Jayaraman | 2003/0097088 A1 | 5/2003 | Pacetti |
| 6,645,135 B1 | 11/2003 | Bhat | 2003/0097173 A1 | 5/2003 | Dutta |
| 6,645,195 B1 | 11/2003 | Bhat et al. | 2003/0099712 A1 | 5/2003 | Jayaraman |
| 6,652,575 B2 | 11/2003 | Wang | 2003/0105518 A1 | 6/2003 | Dutta |
| 6,656,216 B1 | 12/2003 | Hossainy et al. | 2003/0113439 A1 | 6/2003 | Pacetti et al. |
| 6,656,506 B1 | 12/2003 | Wu et al. | 2003/0150380 A1 | 8/2003 | Yoe |
| 6,660,034 B1 * | 12/2003 | Mandrusov et al. ......... 623/1.42 | 2003/0157241 A1 | 8/2003 | Hossainy et al. |
| 6,663,662 B2 | 12/2003 | Pacetti et al. | 2003/0158517 A1 | 8/2003 | Kokish |
| 6,663,880 B1 | 12/2003 | Roorda et al. | 2003/0190406 A1 | 10/2003 | Hossainy et al. |
| 6,666,880 B1 | 12/2003 | Chiu et al. | 2003/0207020 A1 | 11/2003 | Villareal |
| 6,673,154 B1 | 1/2004 | Pacetti et al. | 2003/0211230 A1 | 11/2003 | Pacetti et al. |
| 6,673,385 B1 | 1/2004 | Ding et al. | 2004/0018296 A1 | 1/2004 | Castro et al. |
| 6,689,099 B2 | 2/2004 | Mirzaee | 2004/0029952 A1 | 2/2004 | Chen et al. |
| 6,689,350 B2 | 2/2004 | Uhrich | 2004/0047978 A1 | 3/2004 | Hossainy et al. |
| 6,695,920 B1 | 2/2004 | Pacetti et al. | 2004/0047980 A1 | 3/2004 | Pacetti et al. |
| 6,706,013 B1 | 3/2004 | Bhat et al. | 2004/0052858 A1 | 3/2004 | Wu et al. |
| 6,709,514 B1 | 3/2004 | Hossainy | 2004/0052859 A1 | 3/2004 | Wu et al. |
| 6,712,845 B2 | 3/2004 | Hossainy | 2004/0054104 A1 | 3/2004 | Pacetti |
| 6,713,119 B2 | 3/2004 | Hossainy et al. | 2004/0060508 A1 | 4/2004 | Pacetti et al. |
| 6,716,444 B1 | 4/2004 | Castro et al. | 2004/0062853 A1 | 4/2004 | Pacetti et al. |
| 6,723,120 B2 | 4/2004 | Yan | 2004/0063805 A1 | 4/2004 | Pacetti et al. |
| 6,730,064 B2 | 5/2004 | Ragheb et al. | 2004/0071861 A1 | 4/2004 | Mandrusov et al. |
| 6,733,768 B2 | 5/2004 | Hossainy et al. | 2004/0072922 A1 | 4/2004 | Hossainy et al. |
| 6,740,040 B1 | 5/2004 | Mandrusov et al. | 2004/0073298 A1 | 4/2004 | Hossainy |
| 6,743,462 B1 | 6/2004 | Pacetti | 2004/0086542 A1 | 5/2004 | Hossainy et al. |
| 6,746,773 B2 | 6/2004 | Llanos et al. | 2004/0086550 A1 | 5/2004 | Roorda et al. |
| 6,749,626 B1 | 6/2004 | Bhat et al. | 2004/0096504 A1 | 5/2004 | Michal |
| 6,753,071 B1 | 6/2004 | Pacetti et al. | 2004/0098117 A1 | 5/2004 | Hossainy et al. |
| 6,758,859 B1 | 7/2004 | Dang et al. | 2004/0106985 A1 | 6/2004 | Jang |
| 6,759,054 B2 | 7/2004 | Chen et al. | 2004/0172121 A1 | 9/2004 | Eidenschink et al. |
| 6,764,505 B1 | 7/2004 | Hossainy et al. | 2004/0172127 A1 | 9/2004 | Kantor |
| 6,776,796 B2 | 8/2004 | Falotico et al. | 2004/0236415 A1 | 11/2004 | Thomas |
| 6,780,424 B2 | 8/2004 | Claude | 2005/0037052 A1 | 2/2005 | Udipi et al. |
| 6,790,228 B2 | 9/2004 | Hossainy et al. | 2005/0038134 A1 | 2/2005 | Loomis et al. |
| 6,824,559 B2 | 11/2004 | Michal | 2005/0038497 A1 | 2/2005 | Neuendorf et al. |
| 6,861,088 B2 | 3/2005 | Weber et al. | 2005/0043786 A1 | 2/2005 | Chu et al. |
| 6,865,810 B2 | 3/2005 | Stinson | 2005/0049693 A1 | 3/2005 | Walker |
| 6,869,443 B2 | 3/2005 | Buscemi et al. | 2005/0049694 A1 | 3/2005 | Neary |
| 6,878,160 B2 | 4/2005 | Gilligan et al. | 2005/0054774 A1 | 3/2005 | Kangas |
| 6,887,270 B2 | 5/2005 | Miller et al. | 2005/0055044 A1 | 3/2005 | Kangas |
| 6,887,485 B2 | 5/2005 | Fitzhugh et al. | 2005/0055078 A1 | 3/2005 | Campbell |
| 6,890,546 B2 | 5/2005 | Mollison et al. | 2005/0060020 A1 | 3/2005 | Jenson |
| 6,890,583 B2 | 5/2005 | Chudzik et al. | 2005/0064088 A1 | 3/2005 | Fredrickson |
| 6,899,731 B2 | 5/2005 | Li et al. | 2005/0065501 A1 | 3/2005 | Wallace |
| 7,008,667 B2 | 3/2006 | Chudzik et al. | 2005/0065545 A1 | 3/2005 | Wallace |
| 7,229,471 B2 * | 6/2007 | Gale et al. ................. 623/1.15 | 2005/0065593 A1 | 3/2005 | Chu et al. |
| 2001/0007083 A1 | 7/2001 | Roorda | 2005/0074406 A1 | 4/2005 | Couvillon, Jr. et al. |
| 2001/0029351 A1 | 10/2001 | Falotico et al. | 2005/0074545 A1 | 4/2005 | Thomas |

| | | | |
|---|---|---|---|
| 2005/0075714 A1 | 4/2005 | Cheng et al. | |
| 2005/0079274 A1 | 4/2005 | Palasis et al. | |
| 2005/0084515 A1 | 4/2005 | Udipi et al. | |
| 2005/0095267 A1 | 5/2005 | Campbell et al. | |
| 2005/0106210 A1 | 5/2005 | Ding et al. | |
| 2005/0113903 A1 | 5/2005 | Rosenthal et al. | |
| 2006/0058868 A1* | 3/2006 | Gale et al. | 623/1.15 |
| 2006/0115514 A1* | 6/2006 | Gengrinovitch | 424/423 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/62630 | 10/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 03 080147 A1 * | 10/2003 |
| WO | WO 04/000383 | 12/2003 |
| WO | WO 2004/009145 | 1/2004 |
| WO | WO 2005/117832 | 12/2005 |
| WO | WO 2005117832 A1 * | 12/2005 |
| WO | WO 2006/056984 | 6/2006 |
| WO | WO 2006/112932 | 10/2006 |
| WO | WO 2006112932 A2 * | 10/2006 |
| WO | WO 2007/097887 | 8/2007 |

OTHER PUBLICATIONS

Steadman's Medical Dictionary, 27th Ed. (Lippincott Williams, 2000, definition of "amphiphilic").*
Saito et al., J Bone Joint Surg Am. 2001;83-A Suppl 1 (pt 2):S92-8, Abstract Only.*
Hersel et al., Biomaterials. 2003;24(24):4385-4415.*
Biochim Biophys Acta. Feb. 25, 1991;1062(2):142-8, Abstract Only.*
Parrish et al., J. Am. Chem. Soc. Epub Apr. 29, 2005; 127:7404-7410.*
U.S. Appl. No. 10/871,658, Hossainy et al.
Anonymous, *Cardiologists Draw—Up the Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Blindt et al., *Abciximab Inhibits the Migration and Invasion Potential of Human Coronary Artery Smooth Muscle Cells*, J. Mol. Cell Cardiol 32, 2195-2206 (2000).
Chung et al., *Inner core segment design for drug delivery control of thermo-responsive polymeric micelles*, Journal of Controlled Release 65:93-103 (2000).
Chung et al., *Enhancing growth human endothelial cells on Arg-Gly-Asp (RGD) embedded poly (∈caprolactone) (PCL) surface with nanometer scale of surface disturbance*, Wiley Periodicals, Inc 213-219 (2004).
Coller, *Anti-GPIIb/IIIa Drugs: Current Strategies and Future Directions*, Thomb Haemost 86, 427-43 (2001).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Fittkau et al., *The selective modulation of endothelial cell mobility on RGD peptide containing surfaces by YIGSR peptides*, Biomaterials 26, 167-174 (2005).
Gombotz et al., *Biodegradable Polymers for Protein and Peptide Drug Delivery*, Bioconjugate Chem. 6, 332-351 (1995).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Kipshidze et al., Role of the Endothelium in Modulating Neointimal Formation, J. of Am. College of Cardiology, vol. 44, No. 4, 734-739 (2004).

Kouvroukoglou et al., *Endothelial cell migration on surfaces modified with immobilized adhesive peptides*, Biomaterials 21, 1725-1733 (2000).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Lutolf et al., *Synthesis and Physicochemical Characterization of End-Linked Poly(ethylene glycol)-co-preptide Hydrogels Formed by Michael-Type Addition*, Biomacromolecules 4, 713-722 (2003).

Mann et al., *Cell adhesion peptides alter smooth muscle cell adhesion, proliferation, migration, and matrix protein synthesis on modified surfaces and in polymer scaffolds*, John Wiley & Sons, Inc. 86-93 (2002).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nam et al., *Intracellular drug delivery using poly(D,L-lactide-co-glycolide) nano-particles derivatized with a peptide from a transcriptional activator protein of HIV-1*, Biotechnology Letters 24: 2093-2098 (2002).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Ruoslahti et al., *New Perspectives in Cell Adhesion:RGD and Integrins*, Science vol. 238, 491-497 (1987).

Saotome, et al., *Novel Enzymatically Degradable Polymers Comprising α-Amino Acid, 1,2-Ethanediol, and Adipic Acid*, Chemistry Letters, pp. 21-24, (1991).

Sajid et al., $α_vβ_3$—*Integrin antagonists inhibit thrombin-induced proliferation and focal adhesion formation in smooth muscle cells*, Am. J. Physiol Cell Physiol 285, C1330-C1338, (2003).

Serruys et al., A Randomized Comparison of the Value of Additional Stenting After Optimal Balloon Angioplasty for Long Coronary Lesions, J. of Am. College of Cardiology, vol. 39, No. 3, 393-399 (2002).

Shigeno, *Prevention of Cerebrovascular Spasm by Bosentan, Novel Endothelin Receptor*, Chemical Abstract 125:212307 (1996).

Srivatsa et al., *Selective α vβ3 integrin blockade potently limits neointimal hyperplasia and lumen stenosis following deep coronary arterial stent injury: Evidence for the functional importance of integrin α vβ3 and osteopontin expression during neointima formation*, Cardiovascular Research 36, 408-428 (1997).

va Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

International Search Rep. for PCT/US2007/014045, filed Jun. 14, 2007, mailed Apr. 25, 2008, 16 pgs.

Hersel et al. "GRD modified polymers: biomaterials for stimulated cell adhesion and beyond", Biomaterials vol. 24, No. 24, pp. 4385-4415 (2003).

Saito et al., J. Bone Joint Surg. Am. 83-A Suppl. 1 (pt 2):S92-8, (2001) Abstract only.

Steadman's Medical Dictionary, 27th Ed. (Lippincott Williams, definition of "amphipathic") (2000).

\* cited by examiner

RGD PEPTIDE ATTACHED TO BIOABSORBABLE STENTS

BACKGROUND

1. Field of the Invention

This invention is generally related to bioabsorbable devices having RGD attached thereto.

2. Description of the State of the Art

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of the arterial lining and to reduce the chance of thrombosis or restenosis, a stent is implanted in the artery to keep the artery open.

Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, ISR still poses a significant problem given the large volume of coronary interventions and their expanding use. The pathophysiological mechanism of ISR involves interactions between the cellular and acellular elements of the vessel wall and the blood. Damage to the endothelium during PCI constitutes a major factor for the development of ISR (see, e.g., Kipshidze, N., et al., J. Am. Coll. Cardiol. 44:733-739 (2004)).

The polypeptide Arg-Gly-Asp (RGD) has been demonstrated to be a bioactive factor for human endothelial cell attachment. It also has been shown that on a polymer surface having RGD chemically bonded to the surface, the growth rate of human endothelial cells can be increased (see, Ruoslahti, E., et al. Science 238:491-497 (1987)). However, this study fails to take into account the accessibility of the RGD to the endothelial progenitor cells (EPCs) so that the endothelial cell growth enhancing effect described therein is limited.

Therefore, there is a need for an attractant attached to a surface for endothelial progenitor cells.

There is a further need for an attractant attached to a surface that provides for improved accessibility of the attractant.

The embodiments of the present invention address these concerns as well as others that are apparent to one having ordinary skill in the art.

SUMMARY

Provided herein is a bioabsorbable stent including a chemo-attractant for endothelial progenitor cells (EPCs). The chemo-attractant is chemically bonded to the bioabsorbable stent via a spacer compound. In some embodiments, the spacer compound comprises a hydrophobic moiety and a hydrophilic moiety. The spacer compound can be grafted to the surface of the bioabsorbable stent. The hydrophobic moiety can be embedded in the stent, and the chemo-attractant can be attached to the hydrophilic moiety. Upon implantation, the hydrophilic moiety can be projected from the surface of the medical device toward a physiologic environment. The chemo-attractant can then recruit EPCs so as to enhance the growth rate of endothelium on the surface of the device. It is important to note that a linker of this construct allows for more freedom for EPCs to access to the chemo-attractant so that the regeneration rate of endothelium on the surface can be enhanced.

In some embodiments, the medical device described herein can further include a bioactive agent. Some examples of the bioactive agent include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40 O-tetrazole-rapamycin, 40-epi-(N1-tetrazolyl)-rapamycin (ABT-578), pimecrolimus, imatinib mesylate, midostaurin, clobetasol, mometasone, CD-34 antibody, abciximab (REOPRO), progenitor cell capturing antibody, prohealing drugs, prodrugs thereof, co-drugs thereof, or a combination thereof.

The medical device described herein can be formed on a medical device for treating, preventing, or ameliorating a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

Figure 1:
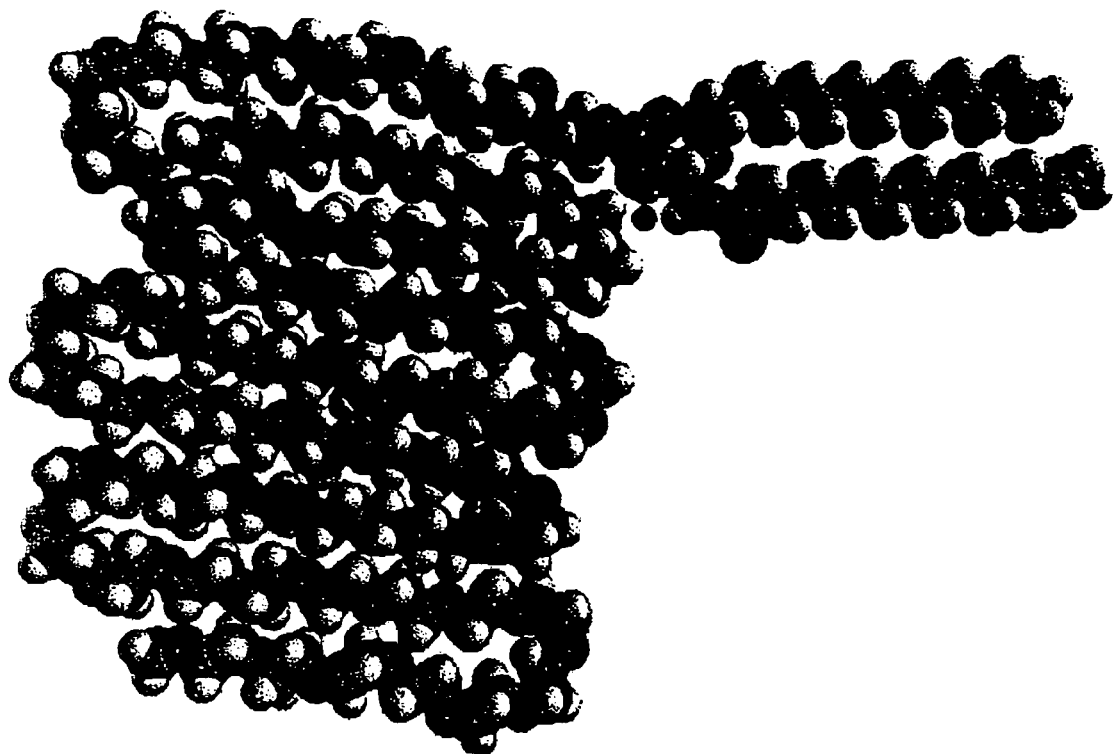
FIG. 1 is a three-dimensional conformation of DMPE-PEG 3000 (1,2-dimyristoyl-sn-glycero-3-phosphoethanolamine-N-[methoxy(polyethylene glycol)-3000])

Provided herein is a bioabsorbable stent including a chemo-attractant for endothelial progenitor cells (EPCs). The chemo-attractant is chemically bonded to the bioabsorbable stent via a spacer compound. In some embodiments, the spacer compound comprises a hydrophobic moiety and a hydrophilic moiety. The spacer compound can be grafted to the surface of the bioabsorbable stent. The hydrophobic moiety can be embedded in the stent, and the chemo-attractant can be attached to the hydrophilic moiety. Upon implantation, the hydrophilic moiety can be projected from the surface of the medical device toward a physiologic environment. The chemo-attractant can then recruit EPCs so as to enhance the growth rate of endothelium on the surface of the device. It is important to note that a spacer compound of the present invention allows for more freedom for EPCs to access to the chemo-attractant so that the regeneration rate of endothelium on the surface can be enhanced.

In some embodiments, the medical device described herein can include a bioactive agent. Some examples of the bioactive agent include siRNA and/or other oligonucleotides that inhibit endothelial cell migration. The bioactive agent can also be lysophosphatidic acid (LPA) or sphingosine-1-phosphate (SIP). LPA is a "bioactive" phospholipid able to generate growth factor-like activities in a wide variety of normal and malignant cell types. LPA plays an important role in normal physiological processes such as wound healing, and in vascular tone, vascular integrity, or reproduction. Some other exemplary bioactive agents are paclitaxel, docetaxel, estradiol, 17-beta-estradiol, nitric oxide donors, super oxide dismutases, super oxide dismutases mimics, 4-amino-2,2,6, 6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy) ethoxy]ethyl-rapamycin, and 40-O-tetrazole-rapamycin, 40-epi-(N1-tetrazolyl)-rapamycin (ABT-578), ÿ-hiridun, clobetasol, pimecrolimus, imatinib mesylate, midostaurin, prodrugs thereof, co-drugs thereof, and combinations thereof.

The medical device such as a stent, can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

Chemo-Attractants

As used herein, the chemo-attractant includes any synthetic or natural molecules capable of attracting endothelial cells. In some embodiments, the chemo-attractant includes any synthetic or natural molecules capable of attracting an effective number of endothelial cells. The attractant generally has a degree of selectivity towards these cells. The chemo-attractant also includes any synthetic or natural molecules capable of binding to adhesion receptors differentially expressed on the endothelial cells. One such adhesion receptor can be integrin. Some exemplary chemo-attractants include, but are not limited to, small integrin-binding molecules, RGD peptide or cyclic RGD peptide (cRGD), synthetic cyclic RGD (cRGD) mimetics, and small molecules binding to other adhesion receptors differentially expressed on the endothelial cells.

In some embodiments, the chemo-attractant can be those molecules capable of binding to ICAM (intercellular adhesion molecule) molecules or VCAM (vascular cell adhesion molecule) molecules, which are present in the endothelial cells. Such chemo-attractant can be, for example, receptors binding to ICAM or VCAM in the endothelial cells, which can include, but are not limited to, Decoy receptor 3 (DcR3), a tumor necrosis factor (TNF) that preferentially binds to ICAM and VCAM_2, integrin LFA-1 (LFA-1Af) (expressed on lymphocytes), which has conformational changes in extracellular domains enabling higher affinity binding to the ligand ICAM-1, or combinations thereof.

In some embodiments, the chemo-attractant can specifically exclude a particular chemo-attractant described above.

cRGD or RGD Mimetics

The cRGD or RGD mimetics described herein includes any peptides or peptide mimetics that result from the modification of the cyclic Arg-Gly-Asp peptide. The modification can be on the pendant groups and/or on the backbone of the peptide. Peptide synthesis, including the synthesis of peptide mimetics, is well documented and can be readily achieved using, for example, combinatorial chemistry.

Some examples of cRGD or RGD mimetics include v3 antagonists such as IIb/IIIb antagonists (Coller, B. S., Thromb. Haemost. 86(1):427-43 (2001) (Review)), one example of which is Abciximax (Blindt, R., J. Mol. Cell. Cardiol. 32:2195-2206 (2000)), XJ 735 (Srivatsa, S. S., et al., Cardiovasc. Res. 36:408-428 (1997)), anti-$_3$-integrin antibody F11, cRGD (Sajid, M., et al., Am. J. Physiol. Cell Physiol., 285:C1330-1338 (2003), and other sequences such as laminin derived SIKVAV (Fittkau, M. H., et al., Biomaterials, 26:167-174 (2005)), laminin derived YIGSR (Kouvroukoglou, S., et al., Biomaterials, 21:1725-1733 (2000)), KQAGDV, and VAPG (Mann, B. K., J. Biomed. Mater. Res. 60(1):86-93 (2002)). The following describes a basic procedure for the synthesis of a peptide, including a peptide mimetics:

Before the peptide synthesis starts, the amine end of the amino acid (starting material) is protected with FMOC (9-fluoromethyl carbamate) or other protective groups, and a solid support such as a Merrifield resin (free amines) is used as an initiator. Then, step (1) through step (3) reactions are performed and repeated until the desired peptide is obtained: (1) a free amine is reacted with the carboxyl end using carbodiimide chemistry, (2) the amino acid sequence is purified, and (3) the protecting group, e.g., the FMOC protecting group, is removed under mildly acidic conditions to yield a free amine. The peptide can then be cleaved from the resin to yield a free standing peptide or peptide mimetic.

In some embodiments, a coating can specifically exclude any of the above mentioned chemo-attractant. For example, a coating can specifically exclude RGD peptide or cyclic RGD peptide (cRGD).

Spacer Compounds

In some embodiments, the spacer compound can have a phospholipid moiety as the hydrophobic moiety. Any phospholipid can be incorporated into the spacer compound. For example, the phospholipid can be phosphatidylcholine, phosphatidylethanolamine, phosphatidic Acid, phosphatidylserine, phosphatidylglycerol, cardiolipin, or phosphatidylinositol.

In some embodiments, the spacer compound can have a hydrophilic moiety which is PEG. In these embodiments, the hydrophobic moiety of the spacer compound can be grafted to or embedded within the surface of the medical device. Upon placed in a physiological environment, the PEG moiety can project from the surface to allow attachment of a chemo-attractant to the PEG moiety. For example, the spacer compound can have a structure of

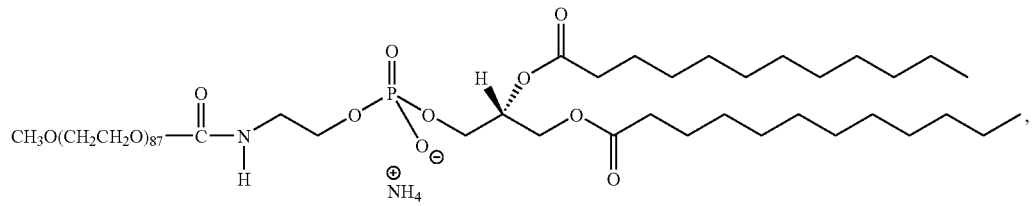

which is DMPE-PEG 3000. Conformational studies on DMPE-PEG 3000 showed that this molecule has a bulk PEG head group and a relatively small phospholipids tail (FIG. 1).

The PEG moiety can have different molecular weights. Generally, the molecular weight of PEG shall be below about 20,000 Daltons so as to allow the PEG to be excreted from the body. Some exemplary ranges of the molecular weight of PEG can be from about 300 Daltons to about 15,000 Daltons, about 1000 Daltons to about 10,000. Daltons, about 2000 Daltons to about 5000 Daltons or about 4000 Daltons.

In some embodiments, the spacer compound can be a di-block copolymer that includes a polymeric hydrophobic block and a polymeric hydrophilic block having a general formula of [hydrophobic polymer]-block-[hydrophilic polymer]. The hydrophobic block can be any hydrophobic polymer. In some embodiments, the hydrophobic polymer can be selected from poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate); poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), polyurethanes, polyalkylene oxalates, polyphosphazenes, or poly(aspirin). In some embodiments, the copolymer described herein can exclude any one of the aforementioned polymers.

The hydrophobic moiety and the hydrophilic moiety shall have a molecular weight or degrade into fragments having a molecular weight ranging from about 20,000 Daltons so as to allow the PEG to be excreted from the body. For example, such a di-blockcopolymer can be poly(L-lactide-co-PEG (3000)).

In some embodiments, the spacer compound can include other hydrophilic moieties. For example, such other hydrophilic moieties can be, poly(alkylene oxide), poly(vinyl alcohol) or poly(ethylene glycol).

Attaching Chemo-Attractant to Hydrophilic Moiety

The chemo-attractant can be attached to the spacer compound described herein via a linkage. The linkage can be degradable or non-degradable. Degradable linkages can be hydrolytically degradable linkages or enzymatically degradable linkages. A hydrolytically degradable linkage can link the chemo-attractant and the spacer compound via the linkage's reactive groups. For example, in some embodiments, the linkage can be an amino acid group that includes amino, thiol, and/or carboxylic groups. Some exemplary strategies for forming hydrolytically degradable linkages include:

(1) ε-Amino group of lysine (which can be integrated into a polymer) and α-amino group of a protein. The amine can be on the polymer backbone (with or without a spacer compound, e.g., PEG, or an alkyl chain). This can yield an amide, thiourea, alkylamine or urethane linkage.
(2) Thiol group or a free cysteine, which forms a thioether linkage.
(3) Thiol group on a cysteine, which can be conjugated with vinylsulfone (R—SO$_2$—CH=CH$_2$).
(4) Carboxylic acid groups on the aspartic and glutamic acid.

Some examples of hydrolytically degradable linkages include amide linkages that can be generated by reacting an amine group with succinate esters such as N-hydroxysuccinimide (NHS), thiol linkages such as disulfide (R-L1-S—S-L2-R') where the length of the linker L1 and L2 control the hydrolization, or ester bonds formed by coupling the peptide's carboxylic end with a hydroxyl on the polymer backbone (with or without a spacer compound, e.g., PEG, or an alkyl chain). Esterification can be carried out using established methods in the art (e.g., carbodiimide chemistry in the presence of 1-ethyl-3-(3-dimethylaminopropyl)carbodiimide (EDC)).

Enzymatically degradable linkages can be degraded by an enzyme, often to target a specific area of the body or organ. In other words, the stimulus for an enzymatically degradable linkage is the presence of an enzyme. For example, a specific dipeptide sequence can be incorporated into the linkage, which can be cleaved by an enzyme. Some examples of enzymatically degradable linkages include, but are not limited to, self-immolative p-aminobenzyloxycarbonyl (PABC)

spacer compound between the dipeptide and the polymer, dipeptides such as phenylaniline-lysine and valine-cysteine, or PEG/dipeptide linkages such as alanyl-valine, alanyl-proline and glycyl-proline.

In some embodiments, the chemo-attractant can be attached to the hydrophilic moiety in the spacer compound by using a photosensitive moiety. In some embodiments, the photosensitive moiety can be, e.g., (N-succinimidyl-6-[4'-azido-2'-nitrophenylamino]-hexanoate). An example of using this photosensitive moiety to attach RGD to PEG is described by Chung et al., J. Biomed. Mater. Res. Part A, vol. 72A(2):213-219 (2005).

Some other linkages can be found at "Biodegradable Polymers for Protein and Peptide Drug Delivery" Bioconjugate Chem. 1995, 6:332-351; M. P. Lutolf and J. A. Hubbell, Biomacromolecules 2003, 4:713-722; and U.S. patent application Ser. No. 10/871,658. Some additional representative linking chemistry is described in U.S. patent application Ser. No. 10/871,658, the entire disclosure of which is hereby incorporated by reference.

Attaching the Spacer Compound to Medical Device

The chemo-attractant can be attached to the spacer compound described prior to or after the spacer compound is applied to the surface of the medical device. In some embodiments, the spacer compound can be applied to the surface of the medical device prior to the surface attachment of the chemo-attractant to the spacer compound. In some embodiments, the spacer compound can be applied to the surface of a medical device after the chemo-attractant is attached to the spacer compound.

The spacer compound can be applied to the surface of a bioabsorbable medical device by an established method of forming a coating. For example, spacer compound can be spray coated onto the surface of a medical device (e.g., a bioabsorbable stent). The spacer compound will then phase separate, with the hydrophobic moiety of the spacer compound being embedded within the surface layer of the medical device and the hydrophilic moiety projecting from the surface of the medical device.

The embedding of the hydrophobic moiety of the spacer compound can be achieved by using an appropriate solvent in coating the spacer compound. For example, the solvent can be chosen so that it can dissolve the spacer compound and dissolve, swell or plasticize a polymer on the surface of the medical device, which can be a coating surface or surface of the medical device itself. The solvent provides the opportunity for the hydrophobic moiety of the spacer compound to entangle with or embed within the top layer of the dissolved, swelled, or plasticized surface of the medical device. The solvent can be a single solvent or a mixture of solvents. In the mixture of solvents, the solvents shall be mutually miscible or substantially miscible. In some embodiments, the solvent can be a mixture of a solvent for the spacer compound and a solvent for a polymer on the surface of the medical device.

Grafting the spacer compound to the medical device can be achieved by the methods revealed in Nam, Y, et al. Biotechnology letters 2093-98 (2002).

In some embodiments, the spacer compound can be attached, embedded or grafted to the surface of a medical device after the chemo-attractant has been attached to the spacer compound via the linkage describe above. The spacer compound with the chemo-attractant can be the spray coated onto the surface of a medical device as described above.

Biocompatible Polymers

The medical device having the features described herein can include any biocompatible polymer. The biocompatible polymer can be biodegradable (both bioerodable or bioabsorbable) or nondegradable and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly (isobutyl methacrylate), poly(tert-butyl methacrylate), poly (n-propyl methacrylate), poly(isopropyl methacrylate), poly (ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly (ether ester), polyalkylene oxalates, polyphosphazenes, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

In some embodiments, the surface layer of the medical device can include a biobeneficial material. The combination can be mixed, blended, or patterned or arranged in separate layers. The biobeneficial material useful in the coatings described herein can be polymeric or non-polymeric. The biobeneficial material is preferably non-toxic, non-antigenic and non-immunogenic enough so that it can be successfully introduced into a patient. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic-acid-bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

Bioactive Agents

In some embodiments, the medical device having the features described herein can optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, or antioxidant properties. These agents can be cystostatic agents, agents that promote the healing of the endothelium (other than by releasing or generating NO), or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Implantable Device

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, endocardial leads (e.g.; FINELINE and ENDOTAK, available from Guidant Corporation, Santa Clara, Calif.), and devices facilitating anastomosis such as anastomotic connectors. The underlying structure of the device can be of virtually any design. The device can include a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device can be, for example, a bioabsorbable stent.

Method of Use

In accordance with embodiments of the invention, a chemo-attractant can be attached to a medical device or prosthesis, e.g., a stent. For a device including one or more active agents, the agent will retain on the device such as a stent during delivery and expansion of the device, and released at a desired rate and for a predetermined duration of time at the site of implantation.

Preferably, the device is a stent. The stent described herein is useful for a variety of medical procedures, including, by way of example, treatment of obstructions caused by tumors in the bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device comprising a chemo-attractant attached to a surface layer of polymer on the medical device, wherein the chemo-attractant is attached to the surface layer through a spacer compound comprising a hydrophobic moiety that comprises a phospholipid and a hydrophilic moiety, and
   wherein the chemo-attractant is attached to the hydrophilic moiety of the spacer compound and the hydrophobic moiety of the spacer compound is grafted to or embedded within the surface layer of polymer on the medical device such that upon deployment of the medical device, the hydrophilic moiety of the spacer compound projects from the surface layer of polymer.

2. The medical device of claim 1, wherein the hydrophilic moiety of the spacer compound comprises poly(ethylene glycol) (PEG).

3. The medical device of claim 1, wherein the phospholipid comprises distearoylphosphatidylethanolamine (DSPE) or 1,2-Dimyristoyl-sn-glycero-3-phosphoethanolamine (DMPE).

4. The medical device of claim 3, wherein spacer compound is DMPE-PEG.

5. The medical device of claim 1, wherein spacer compound is a di-block copolymer,
   wherein the hydrophobic moiety comprises a hydrophobic polymer block, and
   wherein the hydrophilic moiety comprises a hydrophilic polymer block.

6. The medical device of claim 5, wherein the hydrophobic polymer block comprises poly(lactic acid).

7. The medical device of claim 5, wherein the hydrophilic polymer block comprises PEG, poly(alkylene oxide), poly(vinyl alcohol) or combinations of these.

8. The medical device of claim 5, wherein the spacer compound is poly(L-lactide-co-PEG (3000)).

9. The medical device of claim 1, wherein the chemoattractant comprises RGD, cRGD, mimetics thereof, or combinations of these.

10. The medical device of claim 2, wherein the chemoattractant comprises RGD, cRGD, mimetics thereof, or combinations of these.

11. The medical device of claim 3, wherein the chemoattractant comprises RGD, cRGD, mimetics thereof, or combinations of these.

12. The medical device of claim 4, wherein the chemoattractant comprises RGD, cRGD, mimetics thereof, or combinations of these.

13. The medical device of claim 5, wherein the chemoattractant comprises RGD, cRGD, mimetics thereof, or combinations of these.

14. The medical device of claim 6, wherein the chemoattractant comprises RGD, cRGD, mimetics thereof, or combinations of these.

15. The medical device of claim 7, wherein the chemoattractant comprises RGD, cRGD, mimetics thereof, or combinations of these.

16. The medical device of claim 8, wherein the chemoattractant comprises RGD, cRGD, mimetics thereof, or combinations of these.

17. The medical device of claim 9, wherein the chemoattractant comprises cRGD, cRGD mimetics, or combinations of these.

18. The medical device of claim 10, wherein the chemoattractant comprises cRGD, cRGD mimetics, or combinations of these.

19. The medical device of claim 11, wherein the chemoattractant comprises cRGD, cRGD mimetics, or combinations of these.

20. The medical device of claim 12, wherein the chemoattractant comprises cRGD, cRGD mimetics, or combinations of these.

21. The medical device of claim 13, wherein the chemoattractant comprises cRGD, cRGD mimetics, or combinations of these.

22. The medical device of claim 14, wherein the chemoattractant comprises cRGD, cRGD mimetics, or combinations of these.

23. The medical device of claim 15, wherein the chemoattractant comprises cRGD, cRGD mimetics, or combinations of these.

24. The medical device of claim 16, wherein the chemoattractant comprises cRGD, cRGD mimetics, or combinations of these.

25. The medical device of claim 1, wherein the medical device is a bioabsorbable stent.

26. The medical device of claim 9, wherein the medical device is a bioabsorbable stent.

27. The medical device of claim 12, wherein the medical device is a bioabsorbable stent.

28. The medical device of claim 16, wherein the medical device is a bioabsorbable stent.

* * * * *